(12) United States Patent
Scott (10) Patent No.: US 12,171,609 B2
(45) Date of Patent: Dec. 24, 2024

(54) SYSTEM AND METHOD FOR HANDHELD X-RAY POSITIONING FOR DENTAL IMAGES

(71) Applicant: Madison Scott, New Whiteland, IN (US)

(72) Inventor: Madison Scott, New Whiteland, IN (US)

( * ) Notice: Subject to any disclaimer, the term of this patent is extended or adjusted under 35 U.S.C. 154(b) by 195 days.

(21) Appl. No.: 18/156,729

(22) Filed: Jan. 19, 2023

(65) Prior Publication Data

US 2023/0225683 A1 Jul. 20, 2023

Related U.S. Application Data

(60) Provisional application No. 63/301,135, filed on Jan. 20, 2022.

(51) Int. Cl.
| | |
|---|---|
| *A61B 6/10* | (2006.01) |
| *A61B 6/00* | (2006.01) |
| *A61B 6/08* | (2006.01) |
| *A61B 6/51* | (2024.01) |
| *A61B 6/58* | (2024.01) |

(52) U.S. Cl.
CPC .................. *A61B 6/51* (2024.01); *A61B 6/08* (2013.01); *A61B 6/107* (2013.01); *A61B 6/4405* (2013.01); *A61B 6/587* (2013.01)

(58) Field of Classification Search
CPC .. A61B 6/51; A61B 6/08; A61B 6/107; A61B 6/4405; A61B 6/587
See application file for complete search history.

(56) References Cited

U.S. PATENT DOCUMENTS 7,090,395 B2 8/2006 Glazer

OTHER PUBLICATIONS

Ostrander "Take it right the first", www.rdhmag.com, https://www.rdhmag.com/patient-care/article/16408259/take-it-right-the-first-time, Aug. 1, 2018, p. 1-18 (Year: 2018).*
Publication date (Year: 2018).*

* cited by examiner

*Primary Examiner* — David P Porta
*Assistant Examiner* — Mamadou Faye
(74) *Attorney, Agent, or Firm* — Woodard, Emhardt, Henry, Reeves & Wagner, LLP; William A. McKenna (57) ABSTRACT

A paralleling device that attaches to or is integrated with the backscatter shield of a handheld x-ray device. The paralleling device includes a number of ports that receive a rod and hold the rod in a fixed position. The rod is attached to an electronic sensor for use in oral and dental radiography. By fixedly attaching the electronic sensor and rod to the handheld x-ray device, the paralleling device allows dentists, hygienists and other dental assistants to easily configure and place the rod and electronic sensor in the patient's mouth without setting the handheld x-ray device down. The paralleling device also ensures that the electronic sensor and handheld x-ray device are at an appropriate angle relative to one another to allow for proper imaging of a patient's mouth.

20 Claims, 7 Drawing Sheets

SYSTEM AND METHOD FOR HANDHELD X-RAY POSITIONING FOR DENTAL IMAGES

CROSS REFERENCE TO RELATED APPLICATIONS

This application claims the benefit of U.S. Provisional Application No. 63/301,135 filed Jan. 20, 2022 of which is hereby incorporated by reference.

FIELD OF THE INVENTION

The invention relates to handheld dental x-ray devices. Specifically, the invention relates to a paralleling device for handheld dental x-ray devices that properly positions x-ray equipment for dental imaging.

BACKGROUND OF THE INVENTION

Oral and dental radiography is an important tool for dental practices to diagnose and treat a patient's mouth, teeth, and gums. Traditionally, dentists, dental hygienists or other dental assistants (hereinafter "dental professional(s)") used large, bulky x-ray machines that would imprint images onto a film placed in a patient's mouth. This would require the dental professional to place the film in the patient's mouth while simultaneously positioning the large x-ray device in order to obtain the desired image. Once the imaging process was completed, the dental professional would then have to develop the film in order to see the image and diagnose the patient.

Luckily, the technology in this field has improved in many respects. First, the large, bulky x-ray machines have been replaced by portable, handheld x-ray devices. Second, dental professionals no longer have to develop film because filmless radiography has become standard practice. Instead of placing film in a patient's mouth, an electronic sensor is placed behind a patient's teeth. The electronic sensor, such as a charge-couple device (CCD) or a complementary metal oxide semiconductor (CMOS), converts the x-rays into a digital image. Lastly, paralleling devices, such as a Rinn instrument, have been developed to help quickly position the electronic sensor in the patient's mouth for proper alignment of the x-ray and the sensor. The Rinn instrument can also be reconfigured for different placements, which assists dental professionals in placing the sensor in different locations of the patient's mouth for imaging of various target areas.

However, a disconnect attributable to the old large x-ray machines still exists as current standard dental practice still requires the dental professional to set the handheld x-ray device down, place and properly align the electronic sensor using the Rinn instrument or the like, pick the x-ray back up, and properly align the x-ray with the Rinn instrument to ensure the x-ray beam is perpendicular to the sensor to obtain a proper image.

Thus, there is a need for improvement in this field.

SUMMARY OF THE INVENTION

Various embodiments of the present disclosure include paralleling devices that attach to or are integrated with a portable, handheld x-ray device used in modern oral and dental radiography. Handheld x-ray devices include a backscatter shield that helps protect the dental professional from exposure to x-ray radiation. In one form, the paralleling devices of the present disclosure either attach to the circumference of the backscatter shield of the handheld x-ray or are integrated within the backscatter shield. This is accomplished in a number of ways, represented by various embodiments of the present disclosure.

For example, the paralleling device may include a clip and hinge located at opposite positions along the circumference of the paralleling device. The paralleling device is closed around the circumference of the backscatter shield via the hinge and locked into place via the clip. Once the paralleling device is placed on the handheld x-ray, it can be used to assist the dental professional in properly imaging a patient's mouth. Other embodiments will be discussed in more detail below.

The paralleling device includes at least two ports, which may sit opposite each other along the circumference of the paralleling device. The ports are designed to receive and hold a positioning rod. The rod is pulled through the port and remains fixed in place once in position. The rod may be, for example, a Rinn XCP. Accordingly, the rod may be configured in different orientations to allow for proper positioning of the electronic sensor. Once the rod is properly attached to the paralleling device, an electronic sensor can be attached to the rod, if it is not already in place.

Configuring a handheld x-ray device with a paralleling device of the present disclosure allows the dental professional to properly position and place the electronic sensor in the patient's mouth without needing to set down the handheld x-ray, and therefore quickly and easily complete the imaging operation, because the electronic sensor is connected to the handheld x-ray via the paralleling device. Further, the dental professional can place the rod in either the first port or the second port and configure the rod to a proper orientation to allow for imaging of a "Complete Mouth Series." By using the various ports in conjunction with different rod configurations, the dental professional can properly image the lower left, upper left, lower right, and upper right teeth or any other desired location in the patient's mouth.

The paralleling device ensures that the shield of the handheld x-ray device is parallel with the imaging surface of the electronic sensor. Said another way, the paralleling device ensures that the x-ray beam is projected perpendicularly relative to the imaging surface of the electronic sensor. This is important to ensure that the images obtained are of sufficient quality to allow the dental professional to make a proper diagnosis.

Further forms, objects, features, aspects, benefits, advantages, and embodiments of the present invention will become apparent from a detailed description and drawings provided herewith.

DETAILED DESCRIPTION OF THE SPECIFIC EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Various embodiments of the present disclosure include paralleling devices that attach to or are integrated in portable, handheld x-ray devices used in modern oral and dental radiography, such as the KaVo NOMAD Pro 2. Handheld x-ray devices include a backscatter shield that helps protect the dental professional from exposure to x-ray particles. The paralleling devices of the present disclosure either attach to the circumference of the backscatter shield of the handheld x-ray or are integrated within the backscatter shield. The paralleling device includes at least two ports, which may sit opposite each other along the circumference of the paralleling device. The ports are designed to receive and hold a positioning rod, such as a Rinn XCP, which is capable of having multiple configurations. Once the rod is properly attached to the paralleling device, an electronic sensor can be attached to the rod, if it is not already in place. By using the various ports in conjunction with different rod configurations, the dental professional can quickly and easily image the lower left, upper left, lower right, and upper right teeth or any other desired location in the patient's mouth.

Directional references herein are for ease of explanation and are not intended to be limiting.

Figure 1:
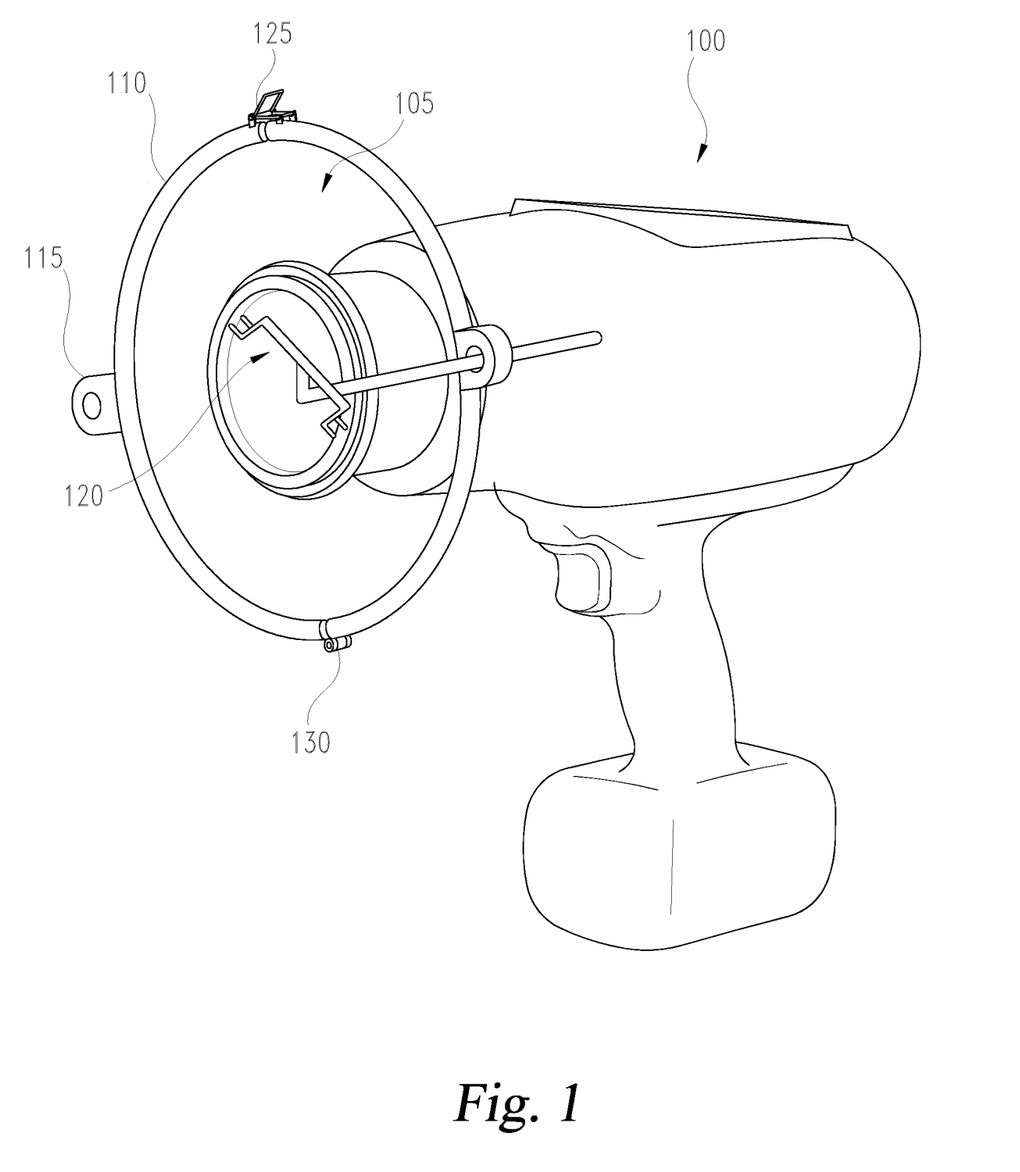
FIG. 1 is a perspective side view of a handheld x-ray device and paralleling device according to an embodiment of the disclosure.

FIG. 1 depicts a representative embodiment of a paralleling device 110 attached to the backscatter shield 105 of a handheld, portable x-ray device 100. The paralleling device 110 connects to the circumference of backscatter shield 105. In this embodiment, the paralleling device 110 has a slightly larger diameter than the backscatter shield 105, sufficient to enable the paralleling device 110 to be closed around the circumference of shield 105. The paralleling device 110 is placed around the circumference of the shield 105 and rotated via hinge 130 until paralleling device 110 is in a closed configuration. The paralleling device 110 is then fixed in place by securing the paralleling device 110 via clip 125.

It should be appreciated that clip 125 may be any type of fastener capable of securing paralleling device 110 to backscatter shield 105. For example, clip 125 may consist of a latch, lock, pin, magnet, clamp or similar locking mechanisms. Similarly, hinge 130 may be any mechanism capable of rotating paralleling device 110 into a closed position around backscatter shield 105. Additionally, paralleling device 110 may be made of any material suitable for use in conjunction with x-rays.

In this embodiment, two ports 115 are located at opposite positions along the circumference of paralleling device 110 (i.e., 180 degrees apart). Notably, ports 115 may be located at any position along the circumference of paralleling device 110, so long as they do not interfere with clip 125, hinge 130, or the other port 115. However, having ports 115 located 180 degrees from each other is ideal as it allows for proper positioning of an electronic sensor in the patient's mouth. Preferably, paralleling device 110 is positioned so that ports 115 are placed at the 3 o'clock and 6 o'clock positions relative to shield 105, as depicted in FIG. 1.

Ports 115 are configured to receive and hold positioning rod 120 in a fixed position. This could be accomplished, for example, by sizing the hole of ports 115 to fit rod 120 perfectly, or by including a friction-inducing material along the inner diameter of ports 115, such as rubber or any other suitable material. Any other suitable method for securing rod 120 in place may also be employed. For example, ports 115 may include additional sets of clips and hinges capable of opening port 115 and closing/securing port 115 around rod 120. As illustrated in FIG. 1, rod 120 may be fixed in either the left port or the right port 115. The appropriate port 115 to use at any give time will depend on the position of the electronic sensor in the patient's mouth, as discussed in more detail below.

Rod 120 may be any suitable instrument for positioning an electronic sensor in a patient's mouth. For example, rod 120 may be a Rinn XCP instrument, or a modified version thereof. Accordingly, rod 120 may be configured in various configurations with the appropriate configuration depending on the x-ray image to be taken. In one modified form, the rod 120 has a specially shaped proximal end to securely fit within port 115. Once rod 120 is properly positioned in port 115, an electronic sensor can be attached to rod 120, if one is not already attached. The electronic sensor (not depicted) may include a charge-coupled device (CCD), a complementary metal oxide semiconductor (CMOS), or any other suitable electronic sensor.

Once the x-ray device 100 is properly equipped with paralleling device 110, rod 120, and an electronic sensor, and rod 120 is properly configured to place the electronic sensor in a desired location, the dental professional can pick up the x-ray device 100, place the rod 120 and the electronic sensor in the patient's mouth and immediately begin imaging. In this way, the dental professional does not need to set the x-ray device 100 down to properly configure rod 120 and then pick up x-ray device 100 to position the x-ray device 100 at an appropriate angle relative to rod 120 and the electronic sensor.

By choosing between ports 115 and changing the configuration of rod 120, the dental professional can properly image every section of a patient's mouth, including upper left, lower left, upper right, and lower right images. Further, the fixed configuration of paralleling device 110 relative to x-ray device 100 allows the dental professional to always keep the x-ray device 100 aligned with the electronic sensor. In this configuration, the shield of x-ray device 100 will always remain parallel to the imaging surface of the electronic sensor in the patient's mouth. Said differently, the x-ray beam will always emanate from x-ray device 100 perpendicular relative to the imaging surface of the electronic sensor as is desired. This ensures that the x-ray imaging results in quality images so the dental professional does not have to expose the patient to additional x-ray radiation and the image will be of sufficient quality to allow for proper diagnosis.

It shall be appreciated in further forms that the ports for holding a positioning rod 120, such as 115, may be integrated into the backscatter shield or elsewhere on the handheld x-ray device to achieve the objective of the present invention and such design is desired to be protected.

Figure 2:
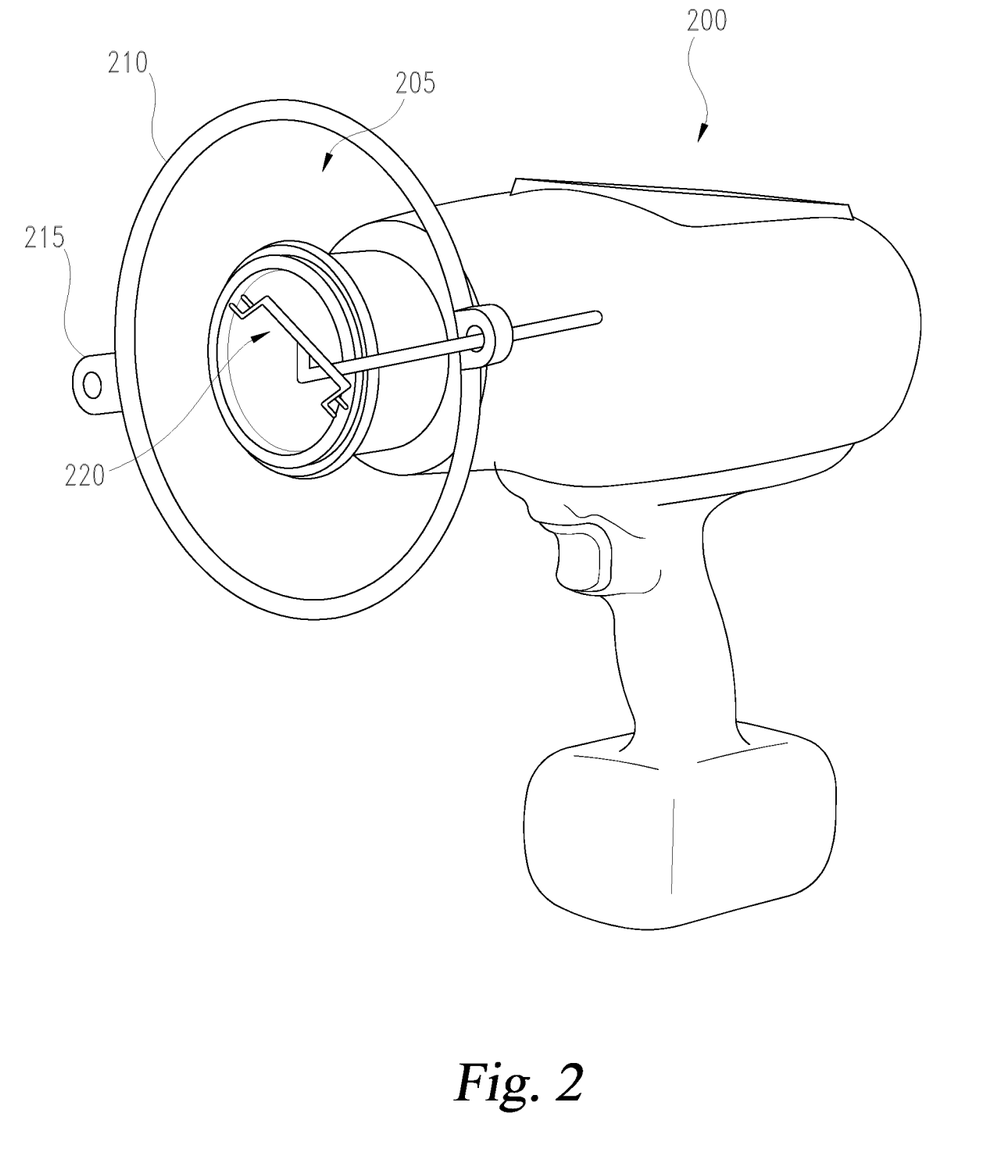
FIG. 2 is a perspective side view of a handheld x-ray device and paralleling device according to a second embodiment of the disclosure.

FIG. 2 depicts an alternative embodiment of the present disclosure. In this embodiment, paralleling device 210 is integrally formed as part of shield 205. This can be accomplished, for example, by forming paralleling device 210 as a part of shield 205 during the manufacturing process. In another form, paralleling device 210 may be permanently affixed to backscatter shield 205. This may be accomplished via industrial adhesives or other similar methods. In other embodiments, paralleling device 210 may rotate around shield 205 via a ratchet-like mechanism, while remaining permanently affixed to shield 205. This configuration would allow a dental professional greater flexibility in positioning the rod 220 by rotating ports 215 around shield 205.

Figure 3:
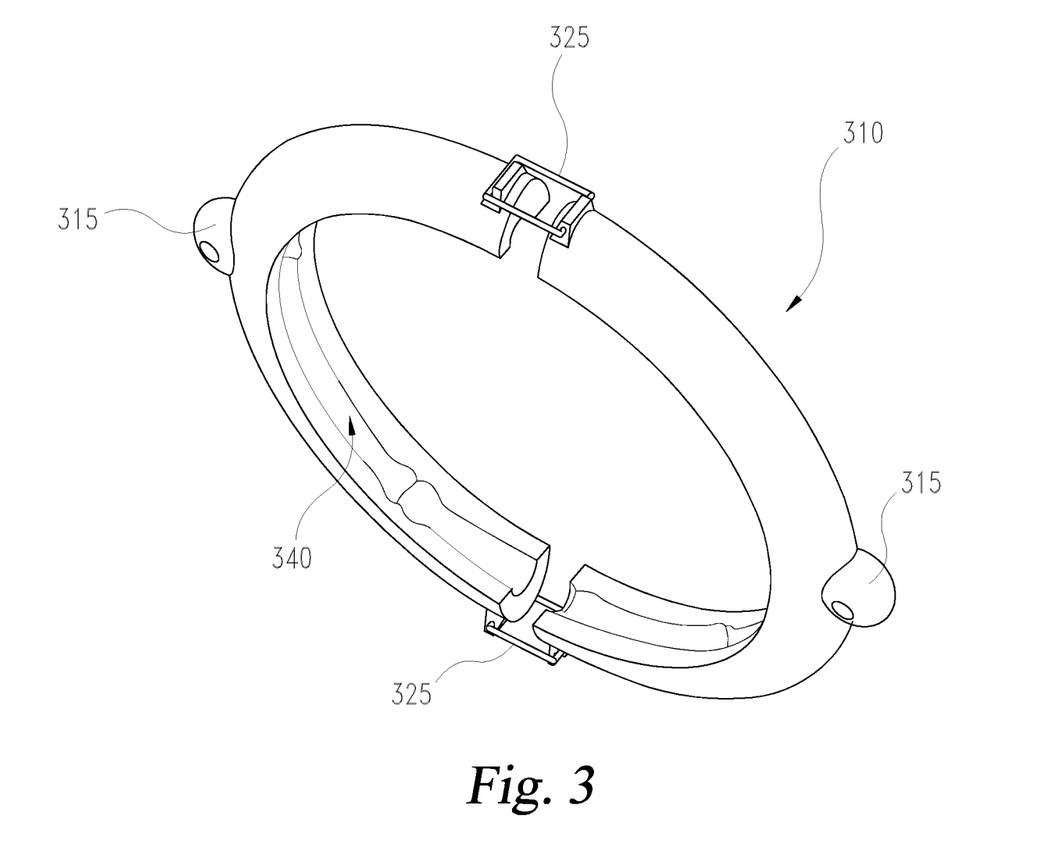
FIG. 3 is a perspective top view of a paralleling device according to a third embodiment of the disclosure.

FIG. 3 illustrates a top perspective view of an embodiment of the present disclosure similar to that depicted in FIG. 1. However, rather than one piece pivoted via hinge 130, paralleling device 310 is comprised of two separate pieces. The two separate pieces of paralleling device 310 are placed around the circumference of a backscatter shield 105, 205 (not depicted in FIG. 3). The pieces of paralleling device 310 are then connected via a pair of clips 325 located 180 degrees apart from each other and 90 degrees apart from ports 315, as shown. It shall be appreciated that alternative connection means may be utilized. FIG. 3 also depicts groove 340, which is formed along the inner circumference of paralleling device 310. Groove 340 allows paralleling device to fit perfectly around the circumference of the backscatter shield 105, 205. All embodiments of the present disclosure may include groove 340. The shape of groove 340 is designed to correspond to the shape of backscatter shield 105, 205.

Figure 4:
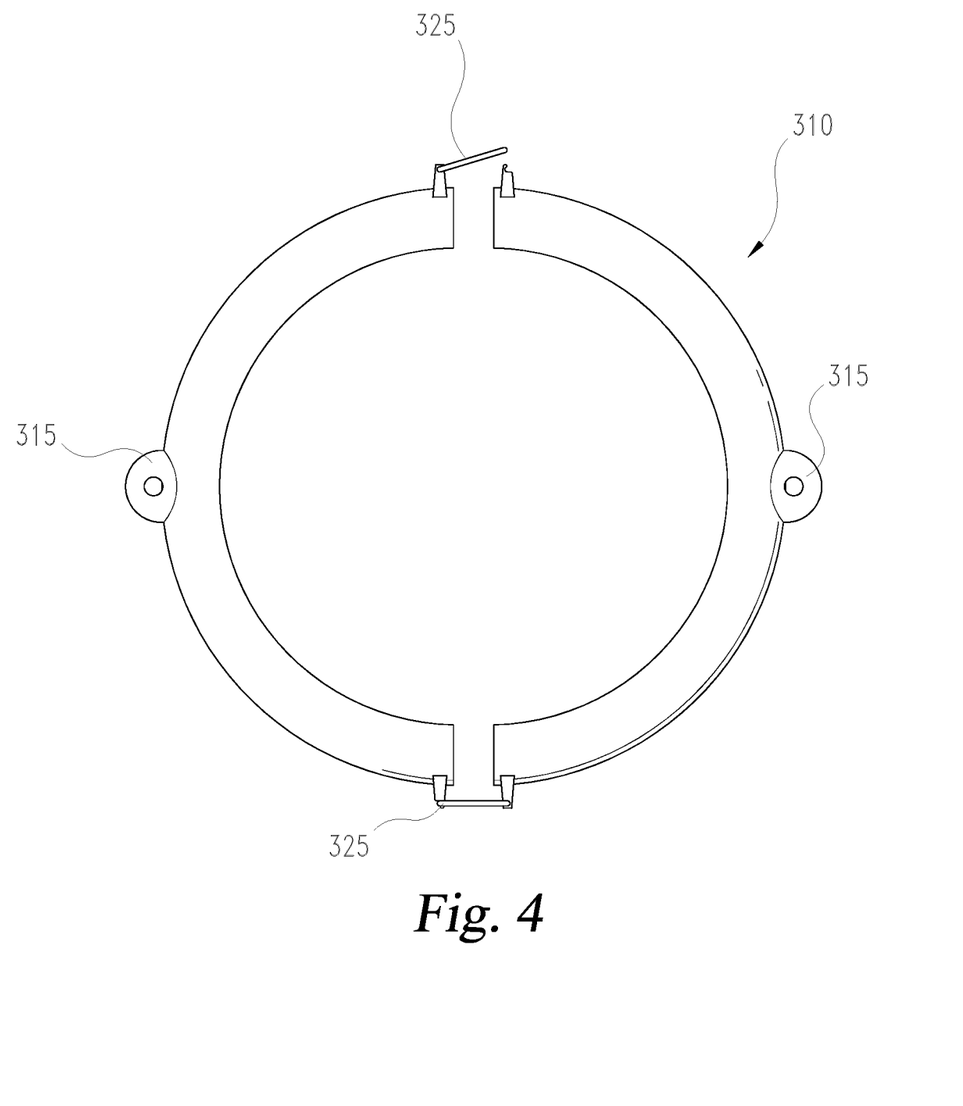
FIG. 4 is a front view of the paralleling device depicted in FIG. 3.

FIG. 4 shows a front view of paralleling device 310. As shown, each piece of paralleling device 310 includes the clip piece of clip 325 on one end and the clip acceptor of clip 325 on the other end.

Figure 5:
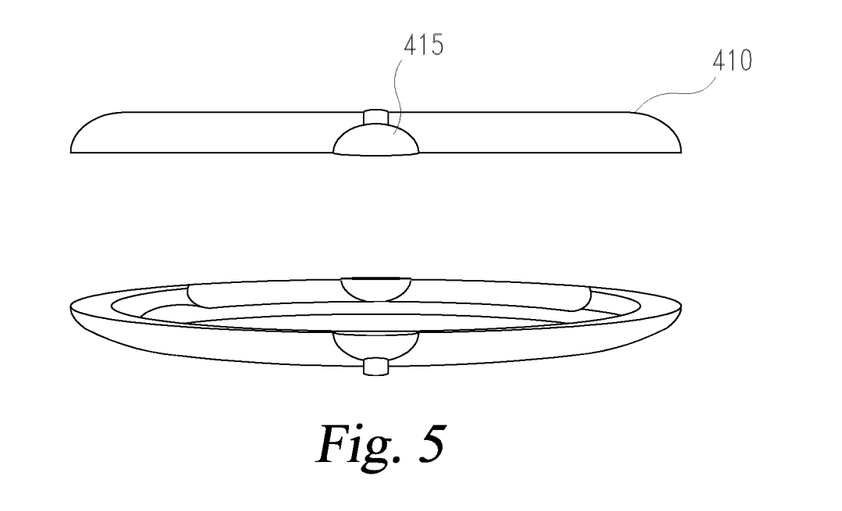
FIG. 5 is a cross-sectional side view of a paralleling device according to a fourth embodiment of the disclosure.

FIG. 5 illustrates another embodiment of a paralleling device 410 wherein paralleling device 410 is configured of two identical pieces that press together to secure around shield 105, 205. Paralleling device 410 can be secured together and around shield 105, 205 in a number of ways. For example, the two pieces may include a snap fit, wherein the pieces are secured when pressed together. Alternatively, paralleling device 410 may include threading so the pieces can be screwed together. In this embodiment, the threading would align the two pieces of paralleling device 410 such that ports 415 would align properly. In some forms, the rearmost piece may be formed from two or more pieces to enable it to be put in place properly.

Figure 6:
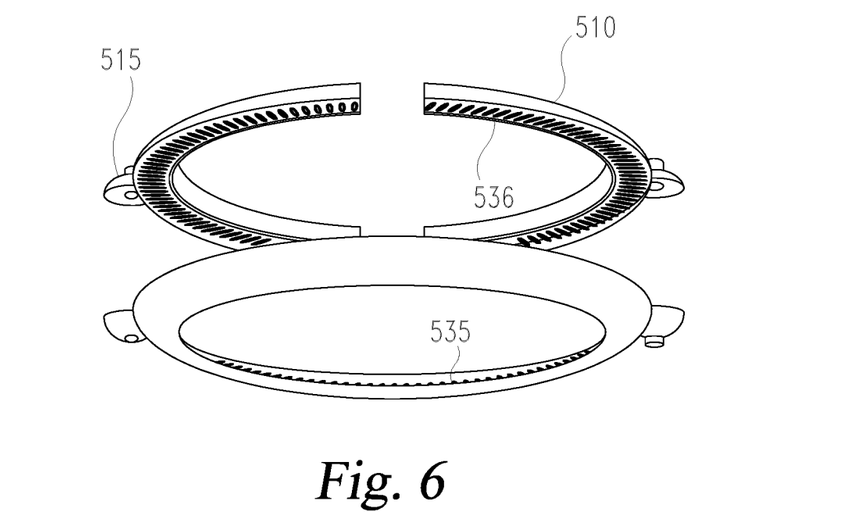
FIG. 6 is a cross-sectional, perspective top view of a paralleling device according to a fifth embodiment of the disclosure.

FIG. 6 illustrates yet another method for securing paralleling device 410, 510 together. In this embodiment, the two pieces of paralleling device 510 contain pins 535 along the inner surface of each piece. Each pin 535 has a corresponding hole 536 located on the opposite piece. When the two pieces of paralleling deice 510 are pushed together, the pins 535 align with their corresponding hole 536 and secure the pieces together. Paralleling device 510 may also optionally include pins 535 and corresponding holes in place of any clips 125 or hinges 130. In this embodiment, either one or both pieces of paralleling device 510 may themselves be comprised of two pieces. As such, paralleling device 510 may include two, three, or possibly four pieces depending on the design implemented.

Figure 7:
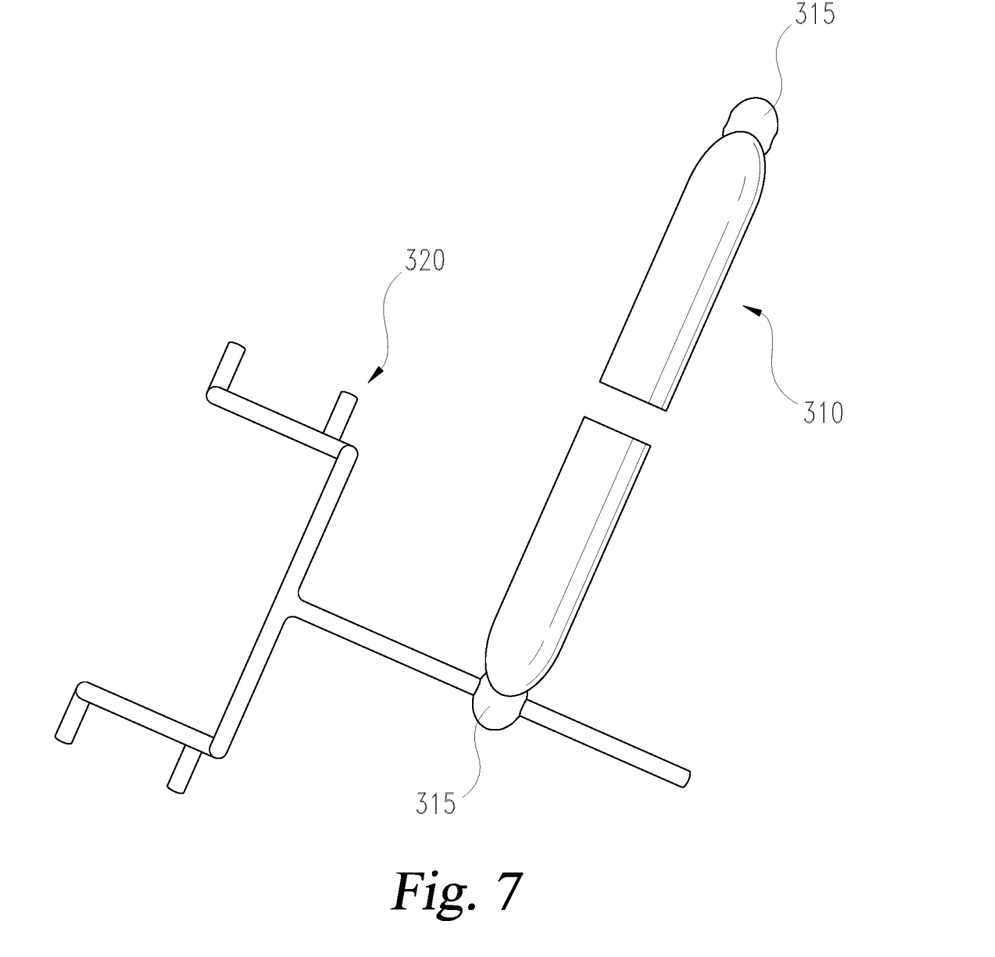
FIG. 7 is an angled top view of a paralleling device of the present disclosure.

FIG. 7 shows a top perspective view of a paralleling device 310. FIG. 7 illustrates the positioning rod 320 within port 315.

Figure 8A:
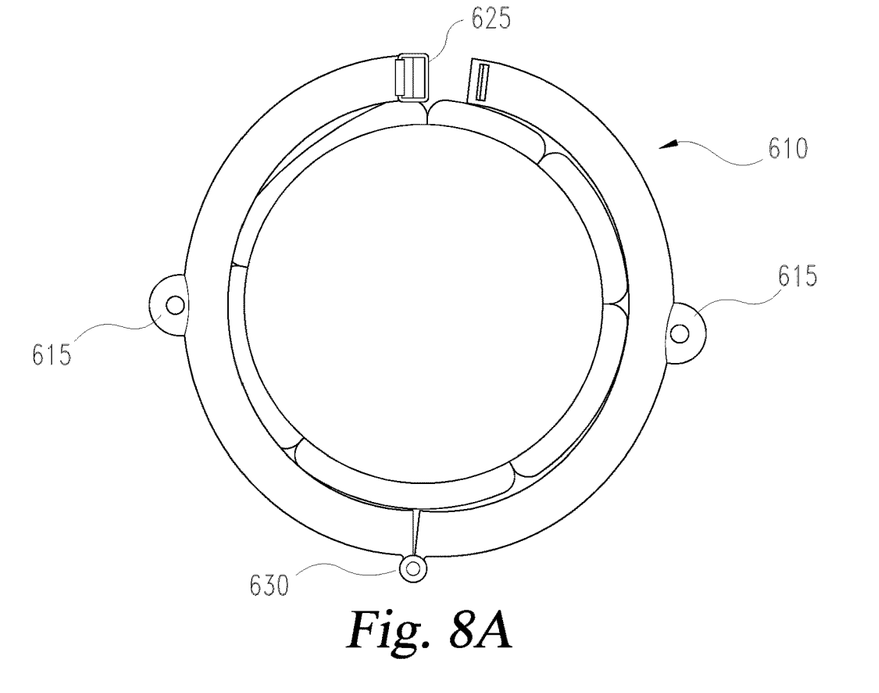
FIG. 8A is a front view of a paralleling device of the present disclosure in an open orientation.
Figure 8B:
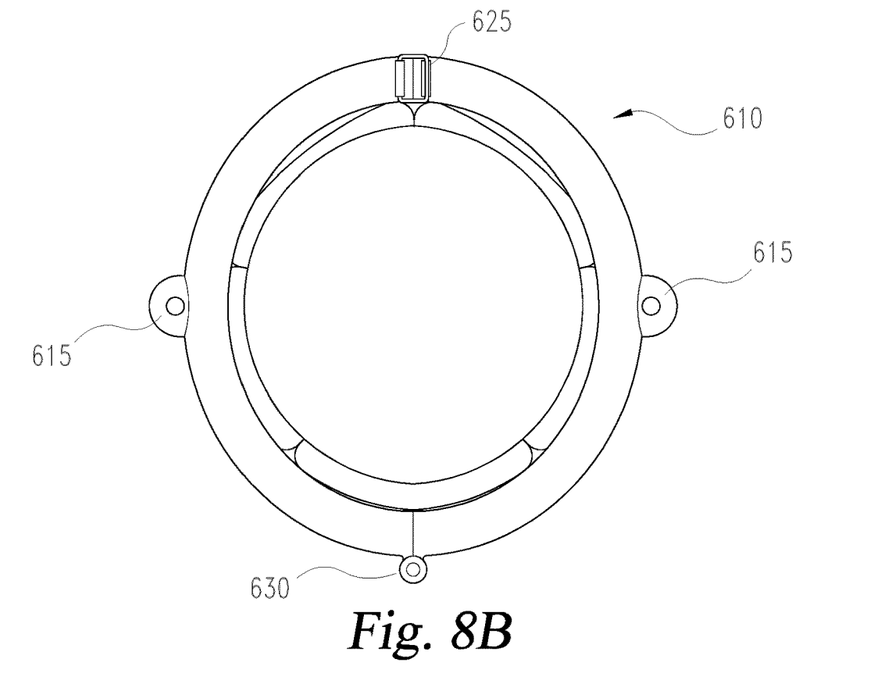
FIG. 8B front view of a paralleling device of the present disclosure in a closed orientation.

FIGS. 8A-8B illustrates a paralleling device 610 contemplated by the present disclosure. Paralleling device 610 is similar to paralleling devices 110, 310, wherein two pieces are connected via a clip 625 and hinge 630 or by two clips 625. However, FIGS. 8A and 8B depicts paralleling device 610 as having a more oval shape than the previously disclosed circular-shape. It should be appreciated that paralleling devices 110 through 610 may take any shape in order to properly be attached or integrated into a backscatter shield 105, 205 of any shape.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A paralleling device for attachment to a backscatter shield on a handheld x-ray device, the paralleling device comprising:
   a paralleling device body including a first body section and a second body section;
   a releasable fastener positioned on said paralleling device body, wherein said releasable fastener is configured to secure said first body section to said second body section; and
   at least one port positioned on said paralleling device body, wherein said at least one port is configured to receive and hold a positioning rod.

2. The paralleling device of claim 1 wherein said port includes a port opening defined through said paralleling device body.

3. The paralleling device of claim 1, wherein the paralleling device includes two ports, and wherein each of said two ports is configured to receive and hold a positioning rod.

4. The paralleling device of claim 2, wherein said two ports are diametrically opposed with respect to each other on said paralleling device body.

5. The paralleling device of claim 1, further comprising:
   a hinge connected between said first body section and said second body section, wherein said hinge allows said first body section to pivot with respect to said second body section.

6. The paralleling device of claim 5, wherein said fastener is positioned on said paralleling device body so that said fastener is diametrically opposed with respect to said hinge.

7. The paralleling device of claim 1, further comprising:
   a positioning rod attached to said paralleling device body at said at least one port; and
   wherein said positioning rod extends perpendicularly from said paralleling device body when attached at said at least one port.

8. The paralleling device of claim 1, wherein said paralleling device body includes an outer perimeter, and wherein said at least one port extends radially outward from said outer perimeter.

9. The paralleling device of claim 1, wherein said first body section of said paralleling device body is separable from said second body section.

10. The paralleling device of claim 9, wherein said first body section includes one of said at least one ports and said second body section includes one of said at least one ports.

11. The paralleling device of claim 1, wherein a groove is defined in an inner surface of said paralleling device body.

12. An x-ray device comprising:
 a backscatter shield configured to protect a user from exposure to x-ray particles;
 a paralleling device positioned around said backscatter shield wherein said paralleling device includes at least one port; and
 a positioning rod attachable to said paralleling device at said at least one port, wherein said positioning rod is configured to hold an electronic sensor for converting x-rays into a digital image.

13. The x-ray device of claim 12, wherein said paralleling device is removably attached to said backscatter shield.

14. The x-ray device of claim 12, wherein said paralleling device is integral to said backscatter shield.

15. The x-ray device of claim 12, wherein said paralleling device includes two ports, and wherein each of said two ports is configured to receive and hold said positioning rod.

16. The x-ray device of claim 15, wherein said two ports are diametrically opposed from each other on said paralleling device.

17. The x-ray device of claim 12, wherein said paralleling device includes a paralleling device body having a first body section and a second body section.

18. The x-ray device of claim 17, wherein said paralleling device includes a releasable fastener positioned on said paralleling device body, and wherein releasable fastener is configured to secure said first body section to said second body section.

19. The x-ray device of claim 18, wherein a hinge is connected between said first body section and said second body section, and wherein said hinge allows said first body section to pivot with respect to said second body section.

20. The x-ray device of claim 18, wherein said first body section is separable from said second body section.

* * * * *